United States Patent
Hatae et al.

(10) Patent No.: US 10,017,534 B2
(45) Date of Patent: Jul. 10, 2018

(54) METHOD FOR PRODUCING TEBBE COMPLEX

(71) Applicant: KURARAY CO., LTD., Kurashiki-shi (JP)

(72) Inventors: Shinji Hatae, Atsugi (JP); Syuichi Sunaga, Kamisu (JP); Tomoaki Tsuji, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 15/514,977

(22) PCT Filed: Sep. 18, 2015

(86) PCT No.: PCT/JP2015/076793
§ 371 (c)(1),
(2) Date: Mar. 28, 2017

(87) PCT Pub. No.: WO2016/052279
PCT Pub. Date: Apr. 7, 2016

(65) Prior Publication Data
US 2017/0218002 A1  Aug. 3, 2017

(30) Foreign Application Priority Data
Sep. 29, 2014  (JP) .................. 2014-198980

(51) Int. Cl.
*C07F 17/00* (2006.01)
*B01J 31/22* (2006.01)

(52) U.S. Cl.
CPC ............ *C07F 17/00* (2013.01); *B01J 31/2295* (2013.01); *B01J 2231/645* (2013.01); *B01J 2531/0208* (2013.01); *B01J 2531/31* (2013.01); *B01J 2531/46* (2013.01)

(58) Field of Classification Search
CPC ............ B01J 31/2295; B01J 2531/0208; B01J 2531/31; C07F 17/00
See application file for complete search history.

(56) References Cited

U.S. PATENT DOCUMENTS

| 5,244,980 A | 9/1993 | Gibler et al. |
| 5,334,566 A | 8/1994 | Gibler et al. |
| 5,886,108 A * | 3/1999 | Miyamoto ............... C08C 19/02 |
| | | 525/332.8 |
| 2006/0287449 A1 | 12/2006 | Miyamoto et al. |

FOREIGN PATENT DOCUMENTS

| JP | 9-278677 A | 10/1997 |
| JP | 11-71426 A | 3/1999 |
| JP | 2000-95814 A | 4/2000 |
| JP | 2004-269665 A | 9/2004 |
| JP | 2005-29731 A | 2/2005 |
| JP | 2009-155402 A | 7/2009 |
| WO | 2012/056939 A1 | 5/2012 |

OTHER PUBLICATIONS

International Search Report dated Dec. 28, 2015 in PCT/JP2015/076793 fled Sep. 18, 2015.
"Olefin Homologation with Titanium Methylene Compounds," Journal of the American Chemical Society, vol. 100, No. 11, 1978, pp. 3611-3613.
Thompson, Rick et al., "Structural Elucidation of the Illustrious Tebbe Reagent," Organometallics, vol. 33, 2014, pp. 429-432.
Ott, Kevin C. et al., "An Investigation of the Reaction of Bis(cyclopentadienyl)titanium Dichlorides with Trimethylaluminum. Mechanism of an α-Hydrogen Abstraction Reaction," Organometallics, vol. 3, No. 2, 1984, pp. 223-230.
Hartley, Richard C. et al., "Titanium carbenoid reagents for converting carbonyl groups into alkenes," Tetrahedron, vol. 63, 2007, pp. 4825-4864.
Haahr, Adam et al., "A one-pot procedure for methylenating carbonyl compounds using the Nysted reagent and titanocene dichloride," Tetrahedron Letters, vol. 52, 2011, pp. 3020-3022.

* cited by examiner

*Primary Examiner* — Pancham Bakshi
(74) *Attorney, Agent, or Firm* — Oblon, McClelland, Maier & Neustadt, L.L.P.

(57) ABSTRACT

The present invention relates to a method for producing a Tebbe complex having high purity and high activity and having excellent storage stability in a high yield, the method including allowing bis(cyclopentadienyl)titanium dichloride and trimethylaluminum to react with each other in the presence of a solvent such that a solubility of the Tebbe complex in 1 g of the solvent at 25° C. is 0.5 mmol/g or less.

11 Claims, No Drawings

US 10,017,534 B2

METHOD FOR PRODUCING TEBBE COMPLEX

TECHNICAL FIELD

The present invention relates to a method for producing a Tebbe complex. In detail, the present invention relates to a method for producing a high-purity Tebbe complex industrially advantageously by allowing bis(cyclopentadienyl)titanium dichloride and trimethylaluminum to react with each other.

BACKGROUND ART

A solution resulting from allowing two molecules of trimethylaluminum ($AlMe_3$) to react with one molecule of bis(cyclopentadienyl)titanium dichloride ($Cp_2TiCl_2$) with each other in a toluene solvent is called a Tebbe reagent, and it is known that a Tebbe complex ($Cp_2TiCH_2AlClMe_2$, µ-chloro-µ-methylene-bis($\eta^5$-cyclopentadienyl)titanium dimethylaluminum) (hereinafter sometimes referred to simply as "Tebbe complex") in this solution is useful as a catalyst component (see, for example, NPLs 1 to 5). In addition, it is also known that the Tebbe complex can be isolated from the Tebbe reagent by carrying out an operation of recrystallization (see PTL 1 and NPLs 1 to 2).

It is known that the Tebbe reagent or Tebbe complex is useful for hydrogenation of an unsaturated double bond of a conjugated diene portion of a conjugated diene polymer (see PTLs 1 to 5), a methylenation reaction of a carbonyl compound, and so on.

It is reported that the high-purity Tebbe complex can be acquired in a purity of 80 to 90% and a yield of 49% by allowing 62 g (0.25 mol) of bis(cyclopentadienyl)titanium dichloride and 48 mL (0.25 mol) of trimethylaluminum to react with each other in 250 mL of toluene at room temperature for 60 hours. Although it is reported that a red-orange crystalline Tebbe complex whose elemental analysis is coincident can be acquired by recrystallizing this crude product from a toluene solution of trimethylaluminum and subsequently pentane, the yield of the foregoing Tebbe complex is not certain (see NPL 1).

Similarly, it is disclosed that bis(cyclopentadienyl)titanium dichloride (0.1 mol) and trimethylaluminum (0.2 mol) are allowed to react with each other in a toluene solvent at room temperature for 60 hours, and a residue from which a volatile component has been distilled off is recrystallized from toluene, whereby 14 g (0.049 mol) of a Tebbe complex can be acquired. Furthermore, it is disclosed that by recrystallizing this from trimethylaluminum-containing toluene and pentane, 9.5 g (0.033 mol) of a red-orange crystalline Tebbe complex having a purity to such an extent that impurities are not observed by $^1$H-NMR analysis can be acquired (see PTL 1).

It is known that a formation rate of the Tebbe complex in the Tebbe reagent varies with an amount of trimethylaluminum relative to titanocene dichloride, a temperature, a time, and a dielectric constant of the solvent (see NPL 3). Furthermore, it is known that a purity of the Tebbe complex is lowered according to the kind of the solvent for depositing a crystal of the Tebbe complex from the Tebbe reagent (see NPL 2).

It is reported that in view of the fact that not only the Tebbe complex contained in the Tebbe reagent is sensitive to air or humidity, but also even if the Tebbe complex is stored in an inert gas atmosphere, it is decomposed, it is preferred to use the Tebbe complex rapidly after preparation (see NPLs 4 to 5). In addition, it is reported that even a single crystal of the Tebbe complex is liable to be decomposed (see NPL 2).

As a method for enhancing the storage stability of the Tebbe complex, there is disclosed a method in which at least one of an oxygen-containing organic compound having 2 or more carbon atoms and a nitrogen-containing compound or a compound composed of a salt thereof is made coexistent relative to a Tebbe complex-containing solution; and it is disclosed that even when the aforementioned Tebbe complex-containing solution having been subjected to chilled storage for 2 months is used for a hydrogenation catalyst of a styrene/butadiene-based block polymer, the catalytic activity does not substantially change (see PTL 1).

CITATION LIST

Patent Literature

PTL 1: JP 09-278677 A
PTL 2: U.S. Pat. No. 5,244,980 A
PTL 3: U.S. Pat. No. 5,334,566 A
PTL 4: JP 11-71426 A
PTL 5: JP 2000-95814

Non-Patent Literature

NPL 1: *Journal of the American Chemical Society*, Vol. 100, No. 11, 1978, pp. 3611-3613
NPL 2: Organometallics, Vol. 33, 2014, pp. 429-432
NPL 3: Organometallics, Vol. 3, No. 2, 1984, pp. 223-230
PTL 4: Tetrahedron, Vol. 63, 2007, pp. 4825-4864
PLL 5: Tetrahedron Letters, Vol. 52, 2011, pp. 3020-3022

SUMMARY OF INVENTION

Technical Problem

Although NPL 1 and PTL 1 describe the production method of the high-purity Tebbe complex, there was involved such a problem that the yield is low.

NPL 3 describes that the dielectric constant of the solvent affects the formation of the Tebbe complex. In addition, NPL 2 describes that the purity of the desired material varies with the solvent to be used for isolation of the Tebbe complex from the Tebbe reagent. However, all of those literatures do not disclose a method of acquiring the high-purity Tebbe complex in a high yield.

As described in NPLs 2, 4, and 5, the Tebbe reagent is low in the storage stability, and in the case of using the Tebbe reagent having been stored for a long period of time, it is necessary to increase the use amount of the catalyst for the purpose of compensating a lowering of the catalytic activity. In the hydrogenation reaction of an unsaturated double bond of a conjugated diene portion of a conjugated diene polymer, in the case of increasing the use amount of the catalyst, there is involved such a problem that an increase of the amounts of a titanium component and an aluminum component contained in a product is caused, whereby yellowing of the product is promoted.

PTL 1 indicates that the Tebbe reagent and the Tebbe complex are low in the storage stability and that as for a method of maintaining the catalytic activity, by making an oxygen-containing organic compound having 2 or more carbon atoms or a nitrogen-containing compound or a salt thereof, or the like coexistent, the catalytic activity can be maintained even after chilled storage for 2 months. However, there is encountered such a problem that the recovery of the solvent becomes complicated because of addition of a minute amount of the oxygen-containing organic compound or the like. Furthermore, the storage stability of the Tebbe complex itself due to the addition of the oxygen-containing organic compound or the like is not clear.

A problem of the present invention is to provide a method for producing a Tebbe complex having high purity and high activity and having excellent storage stability in a high yield.

Solution to Problem

The present inventors have found that a high-purity Tebbe complex can be produced in a high yield by allowing bis(cyclopentadienyl)titanium dichloride and trimethylaluminum to react with each other in the presence of a specified solvent; that it is possible to store a solution of the Tebbe complex (hereinafter sometimes referred to simply as "catalyst liquid") for a long period of time without adding an additive; and that catalytic activity in a hydrogenation reaction of an unsaturated double bond of a conjugated diene portion of a conjugated diene polymer per one titanium atom of the Tebbe complex is high as compared with that of the conventional Tebbe reagent, leading to accomplishment of the present invention.

Specifically, the present invention provides the following [1] to [8].
[1] A method for producing a Tebbe complex, including allowing bis(cyclopentadienyl)titanium dichloride and trimethylaluminum to react with each other in the presence of a solvent such that a solubility of the Tebbe complex in 1 g of the solvent at 25° C. is 0.5 mmol/g or less.
[2] The method for producing a Tebbe complex of the item [1], wherein the solvent is an aliphatic hydrocarbon having 3 to 20 carbon atoms.
[3] The method for producing a Tebbe complex of the item [1] or [2], wherein the aliphatic hydrocarbon having 3 to 20 carbon atoms is at least one selected from a straight-chain aliphatic hydrocarbon having 3 to 20 carbon atoms and a branched aliphatic hydrocarbon having 3 to 20 carbon atoms.
[4] The method for producing a Tebbe complex of any of the items [1] to [3], wherein a charged amount of the trimethylaluminum is one to twenty molecules relative to one molecule of the bis(cyclopentadienyl)titanium dichloride.
[5] The method for producing a Tebbe complex of any of the items [1] to [4], wherein a charged amount of the bis(cyclopentadienyl)titanium dichloride is from 0.1 to 2.5 mmol/g in terms of a titanium atom concentration relative to the solvent.
[6] The method for producing a Tebbe complex of any of the items [1] to [5], wherein a temperature of the reaction between bis(cyclopentadienyl)titanium dichloride and trimethylaluminum is from 0 to 125° C.
[7] The method for producing a Tebbe complex of any of the items [1] to [6], wherein a time of the reaction between bis(cyclopentadienyl)titanium dichloride and trimethylaluminum is from 1 to 200 hours.
[8] The method for producing a Tebbe complex of any of the items [1] to [7], including a step of recovering the Tebbe complex in a solid state as deposited from a reaction solution liquid obtained through the reaction by filtration or decantation.

Advantageous Effects of Invention

In accordance with the present invention, it is possible to provide a method for producing a Tebbe complex having high purity and high activity and having excellent storage stability in a high yield. That is, it is possible to provide a method for producing a Tebbe complex, in which the Tebbe complex having a purity of 90% or more can be produced in a yield of 70% or more. In view of the fact that the Tebbe complex that can be produced according to the present invention has high catalytic activity per one titanium atom as compared with the conventional Tebbe reagent, it is possible to decrease a use amount of the catalyst. Furthermore, it is possible to store the Tebbe complex stably in an inert gas atmosphere for 120 days or more without making an oxygen-containing organic compound having 2 or more carbon atoms or a nitrogen-containing compound or a compound composed of a salt thereof coexistent. Thus, the present invention is high in an industrial value.

DESCRIPTION OF EMBODIMENTS

The present invention is concerned with a method for producing a Tebbe complex, including allowing bis(cyclopentadienyl)titanium dichloride and trimethylaluminum to react with each other in the presence of a solvent such that a solubility of the Tebbe complex in 1 g of the solvent at 25° C. is 0.5 mmol/g or less.

In raw materials of bis(cyclopentadienyl)titanium dichloride ($Cp_2TiCl_2$) and trimethylaluminum ($AlMe_3$) that are used in the production method of the present invention, it is preferred that a hydroxyl compound, such as water, an alcohol, etc., a ketone, and the like, which are liable to decompose the Tebbe complex, are removed. In addition, in the aforementioned raw materials, it is preferred that oxygen is removed with nitrogen, helium, or argon each serving as an inert gas. It is preferred that all of operations according to the present invention are carried out in an atmosphere of nitrogen, helium, or argon each serving as an inert gas. As the bis(cyclopentadienyl)titanium dichloride and trimethylaluminum, commercially available products can be used, and those having a purity of typically 95% or more, and preferably 98% or more are industrially available. In the case of satisfying such a purity, the yield and purity of the Tebbe complex are high owing to the matter that by-products in the reaction can be inhibited.

As for the raw materials that are provided for the reaction between bis(cyclopentadienyl)titanium dichloride and trimethylaluminum, the bis(cyclopentadienyl)titanium dichloride may be in a state of uniform solution, suspension liquid, or solid, and the trimethylaluminum may be diluted with a solvent. Although a procedure of mixing is not particularly limited, a method of feeding trimethylaluminum into a suspension liquid of bis(cyclopentadienyl)titanium dichloride to undergo the reaction; or a method of feeding a suspension liquid of bis(cyclopentadienyl)titanium dichloride into a diluted liquid of trimethylaluminum to undergo the reaction is preferred because the method is simple and easy.

The solvent that is used for allowing bis(cyclopentadienyl)titanium dichloride and trimethylaluminum to react with each other is a solvent that does not substantially react with the Tebbe complex and trimethylaluminum, in which a solubility of the Tebbe complex in 1 g of the solvent at 25° C. is 0.5 mmol/g or less. From the viewpoint of obtaining the Tebbe complex having high purity and high activity and having excellent storage stability in a high yield, the solubility is preferably from 0.1 to 0.4 mmol/g, more preferably from 0.15 to 0.3 mmol/g, and even more preferably from 0.2 to 0.25 mmol/g.

As described in the Examples, the solubility of the Tebbe complex in 1 g of the solvent at 25° C. is one calculated by adding the solvent to the Tebbe complex to prepare a solution and measuring a titanium atom concentration by using the foregoing solution through atomic absorption analysis.

From the viewpoint of obtaining the Tebbe complex having high purity and high activity and having excellent storage stability in a high yield, the solvent according to the production method of the present invention is preferably an aliphatic hydrocarbon having 3 to 20 carbon atoms, more preferably an aliphatic hydrocarbon having 5 to 8 carbon atoms, even more preferably an aliphatic hydrocarbon having 6 or 7 carbon atoms, and further even more preferably an aliphatic hydrocarbon having 6 carbon atoms.

The aliphatic hydrocarbon having 3 to 20 carbon atoms may be any of a straight-chain aliphatic hydrocarbon, a branched aliphatic hydrocarbon, and an alicyclic hydrocarbon, and may be a saturated or unsaturated aliphatic hydrocarbon.

Examples of the straight-chain saturated aliphatic hydrocarbon having 3 to 20 carbon atoms include propane, butane, pentane, hexane, heptane, octane, nonane, n-decane, undecane, dodecane, tridecane, tetradecane, pentadecane, hexadecane, heptadecane, octadecane, and the like.

Examples of the branched saturated aliphatic hydrocarbon having 3 to 20 carbon atoms include isobutane, 2-methylpentane, 3-methylpentane, isopentane, neopentane, 2,3-dimethylbutane, 2-methylhexane, 3-methylhexane, 2,3-dimethylpentane, 2,4-dimethylpentane, 3-ethylpentane, 2-methylheptane, 3-methylheptane, 4-methylheptane, 2,3-dimethylhexane, 2,4-dimethylhexane, 2,5-dimethylhexane, 3,4-dimethylhexane, 2-ethylhexane, 3-ethylhexane, 3-ethyl-2-methylpentane, 2,3,4-trimethylpentane, 2,2,4-trimethylpentane, 2,2,3-trimethylpentane, 2-methyloctane, 3-methyloctane, 3-ethylheptane, 4-ethylheptane, 2,3-dimethylheptane, 2,4-dimethylheptane, 2,5-dimethylheptane, 2,6-dimethylheptane, 2,3,4-trimethylhexane, 2,3,5-trimethylhexane, 3-ethyl-2-methylhexane, 3-ethyl-3-methylhexane, 3-ethyl-4-methylhexane, 3-ethyl-5-methylhexane, 2-methylnonane, 3-methylnonane, 4-methylnonane, 5-methylnonane, 3-ethyloctane, 4-ethyloctane, 5-ethyloctane, 2,3-dimethyloctane, 2,4-dimethyloctane, 2,5-dimethyloctane, 2,6-dimethyloctane, 2,7-dimethyloctane, 2,2-dimethyloctane, 3,3-dimethyloctane, 3,4-dimethyloctane, 3,5-dimethyloctane, 4,4-dimethyloctane, 4,5-dimethyloctane, 5,5-dimethyloctane, 2,3,4-trimethylheptane, 2,3,5-trimethylheptane, 2,3,6-trimethylheptane, 2,2,3-trimethylheptane, 2,2,4-trimethylheptane, 2,2,5-trimethylheptane, 2,2,6-trimethylheptane, 3,3,4-trimethylheptane, 3,3,5-trimethylheptane, 3,3,6-trimethylheptane, 2,4,5-trimethylheptane, 2,4,6-trimethylheptane, 2,5,6-trimethylheptane, 3-ethyl-3-methylheptane, 3-ethyl-4-methylheptane, 3-ethyl-5-methylheptane, 3-ethyl-6-methylheptane, 4-ethyl-4-methylheptane, 4-ethyl-5-methylheptane, 3-propylheptane, 3-isopropylheptane, and the like.

Examples of the saturated alicyclic hydrocarbon having 3 to 20 carbon atoms include cyclopropane, cyclobutane, cyclopentane, cyclohexane, cycloheptane, cyclooctane, and those hydrocarbons substituted with an alkyl substituent having 1 to 5 carbon atoms.

An unsaturated aliphatic hydrocarbon having 3 to 20 carbon atoms, in which a part of the carbon-carbon single bond of the aforementioned straight-chain or branched saturated aliphatic hydrocarbon or saturated alicyclic hydrocarbon is an unsaturated double bond, can also be used.

Examples of the unsaturated aliphatic hydrocarbon having 3 to 20 carbon atoms include alkenes having 3 to 20 carbon atoms, such as propylene, 1-butene, 2-butene, isobutene, 1-pentene, 2-pentene, 1-hexene, 2-hexene, 1-heptene, 2-heptene, 1-octene, 2-octene, 1-nonene, 2-nonene, 1-decene, 2-decene, 1-undecene, etc.; and cycloalkenes having 3 to 20 carbon atoms, such as cyclopentene, cyclohexene, cycloheptene, cyclooctene, etc.

As the aforementioned aliphatic hydrocarbon having 3 to 20 carbon atoms, those hydrocarbons in which a part of hydrogen atoms is substituted with a halogen atom can also be used. Furthermore, these aliphatic hydrocarbons having 3 to 20 carbon atoms may be used solely or may be used in combination of two or more thereof. In the case of using two or more selected from aliphatic hydrocarbons having 3 to 20 carbon atoms, the solubility of the Tebbe complex is expressed in terms of a solubility as the mixed solvent.

The case of using a solvent having a boiling point of 10° C. or higher at atmospheric pressure is economical because it is not necessary to pressurize the reaction system, whereas the case of using a solvent having a boiling point of 125° C. or lower at atmospheric pressure is economical because steam can be used as a heat source for removal of the solvent. As such a solvent, an aliphatic hydrocarbon having 5 to 8 carbon atoms is preferably used. Especially, as the aliphatic hydrocarbon having 5 to 8 carbon atoms, which is industrially available with ease and is also hardly denatured on the occasion of solvent recovery and use, pentane, hexane, heptane, octane, cyclohexane, and the like are preferably used.

On the reaction, it is not necessary that the whole of bis(cyclopentadienyl)titanium dichloride is dissolved in the solvent, and a charged amount of the bis(cyclopentadienyl)titanium dichloride is preferably in the range of from 0.1 to 2.5 mmol/g, and more preferably in the range of from 0.5 to 1.5 mmol/g in terms of a titanium atom concentration relative to the solvent. When the charged amount falls within this range, the Tebbe complex can be selectively deposited in a state of maintaining a good stirring state, so that the yield and purity of the Tebbe complex are high.

A charged amount of the trimethylaluminum is preferably in the range of from one to twenty molecules, and more preferably in the range of from two to five molecules relative to one molecule of the bis(cyclopentadienyl)titanium dichloride. When the charged amount falls within this range, not only the yield of the Tebbe complex is high, but also the use amount of the trimethylaluminum can be decreased.

In order to suitably carry out the reaction, conditions of temperature and pressure under which trimethylaluminum (boiling point: 125° C.) and chlorodimethylaluminum (boiling point: 126 to 127° C.) as a by-product are made existent in a liquid phase are preferred.

The reaction temperature is preferably from 0 to 125° C., and more preferably 10 to 50° C. When the reaction temperature falls within this range, the reaction time can be shortened, and the Tebbe complex can be obtained in a high yield.

The reaction may be performed in an inert gas atmosphere of nitrogen, argon, helium, or the like, from which moisture and oxygen have been removed. Although the reaction pressure is not limited, for the purpose of removing a by-produced methane gas, the pressure is preferably normal pressure to 0.5 MPaG, and if desired, the inert gas within the system may be substituted with a fresh inert gas.

The reaction time may be controlled in such a manner that the yield of the Tebbe complex becomes maximum, and it is preferably in the range of from 1 to 200 hours, and more preferably in the range of from 24 to 100 hours. When the reaction time falls within this range, the Tebbe complex can be obtained in a high yield.

The production method of the present invention can be carried out using a jacketed complete mixing type reactor. The material of the reactor may be iron, stainless steel, Hastelloy C, titanium, or the like, and those reactors in which an inner wall thereof is glass-lined can also be used. From the standpoint of avoiding contamination of a metal ion to be caused due to the reactor into the desired material, a reactor in which an inner wall thereof is glass-lined is preferably used.

The production method of the present invention can be chosen from two kinds of modes of a batch system (inclusive of a semi-continuous system) and a continuous flow-through system, and as the case may be, the production method can also be carried out in a continuous flow-through system through connection of those 2 to 3 complete mixing type reactors in series. What the production of the Tebbe complex is carried out by a single reactor results in simplification of equipment, and therefore, it is preferred to carry out the production in a batch system (inclusive of a semi-continuous system).

The Tebbe complex in a solid state is contained in the obtained reaction liquid, and by subjecting the reaction liquid to a separation operation, such as filtration, decantation, etc., the solution containing impurities and the Tebbe complex can be separated from each other. From the viewpoint of obtaining the Tebbe complex having high purity and high activity and having excellent storage stability in a high yield, it is preferred that the production method of the present invention includes a step of recovering the Tebbe complex in a solid state as deposited from the reaction liquid obtained through the reaction by means of filtration or decantation. In the step of recovering the Tebbe complex, filtration and decantation may be properly combined, and for example, there may be adopted a method in which the Tebbe complex in a solid state, which is existent within the reaction liquid, is first precipitated, and a supernatant solution containing impurities is removed by means of decantation, and subsequently, filtration is performed.

For the purpose of increasing the yield of the Tebbe complex, the reaction liquid may be concentrated. The concentration can be carried out using a reactor similar to that used for preparing the Tebbe complex, and a thin film type concentrator or the like can also be used. In the case of performing the concentration at high temperature, the yield decreases with thermal decomposition of the Tebbe complex, and therefore, it is preferred to perform the concentration under a condition of the reaction temperature or lower. The concentration temperature is preferably from 10 to 125° C., and more preferably from 20 to 50° C. The concentration pressure is in the range of preferably from 0.001 to 0.100 MPaG (meaning a gauge pressure; hereinafter the same), and more preferably 0.003 to 0.020 MPaG. When the concentration pressure falls within this range, not only the decomposition of the Tebbe complex can be inhibited, but also the concentration time can be shortened, and the yield is high.

For the purpose of increasing the yield of the Tebbe complex, it is preferred to subject the reaction liquid to a crystallization operation. A crystallization temperature is in the range of preferably from −10 to 20° C., and more preferably 0 to 10° C. A crystallization time is preferably 30 minutes or more, and more preferably 1 to 2 hours.

When the reaction liquid having been subjected to a crystallization operation is subjected to filtration or decantation, the Tebbe complex can be separated from the solution containing impurities.

For the purpose of increasing the purity of the Tebbe complex, the separated Tebbe complex may be washed with a hydrocarbon solvent. A dielectric constant of the hydrocarbon solvent that is used for washing is preferably in the range of from 1.0 to 5.0. Furthermore, a temperature of the hydrocarbon solvent is preferably in the range of from −10 to 20° C., and more preferably in the range of from 0 to 10° C. By using such a hydrocarbon solvent, the purity can be increased without impairing the yield.

In the Tebbe complex obtained by the production method of the present invention, the purity may be increased by adding a hydrocarbon solvent, such as an aliphatic hydrocarbon, an aromatic hydrocarbon, etc., such that a titanium atom concentration of the Tebbe complex is in the range of from 0.1 to 2.5 mmol/g, and more preferably from 0.5 to 1.5 mmol/g, and dissolving the Tebbe complex at ranging from 0 to 125° C., and more preferably ranging from 10 to 50° C., and further subjecting to crystallization and washing operations, if desired.

The Tebbe complex obtained by the production method of the present invention may be stored in a state of either a solid state or a solution state so long as an inert gas is present. The solvent that is used for the preparation of a solution is not particularly limited so long as it does not substantially react with the Tebbe complex, and the solvent that is used for the reaction of bis(cyclopentadienyl)titanium dichloride and trimethylaluminum can also be used. As the solvent that is used for the preparation of a solution, there may also be used aromatic hydrocarbons, such as benzene, toluene, ethylbenzene, propylbenzene, butylbenzene, o-xylene, m-xylene, p-xylene, etc.; acyclic monoethers, such as dimethyl ether, methyl ethyl ether, diethyl ether, ethyl-n-propyl ether, di-n-propyl ether, n-butyl methyl ether, tert-butyl methyl ether, di-n-butyl ether, di-n-octyl ether, ethyl phenyl ether, diphenyl ether, etc.; acyclic diethers, such as 1,2-dimethoxyethane, 1,2-diethoxyethane, 1,2-diisopropoxyethane, 1,2-butoxyethane, 1,2-diphenoxyethane, 1,2-dimethoxypropane, 1,2-diethoxypropane, 1,2-diphenoxypropane, 1,3-dimethoxypropane, 1,3-diethoxypropane, 1,3-disopropoxypropane, 1,3-dibutoxypropane, 1,3-diphenoxypropane, cyclopentyl methyl ether, etc.; cyclic ethers, such as tetrahydrofuran, tetrahydropyran, 1,4-dioxane, 2-methyltetrahydrofuran, etc.; acyclic polyethers, such as diethylene glycol dimethyl ether, dipropylene glycol dimethyl ether, dibutylene glycol dimethyl ether, diethylene glycol diethyl ether, dipropylene glycol diethyl ether, dibutylene glycol diethyl ether, triethylene glycol dimethyl ether, tripropylene glycol dimethyl ether, tributylene glycol dimethyl ether, triethylene glycol diethyl ether, tripropylene glycol diethyl ether, tributylene glycol diethyl ether, tetraethylene glycol dimethyl ether, tetrapropylene glycol dimethyl ether, tetrabutylene glycol dimethyl ether, tetraethylene glycol diethyl ether, tetrapropylene glycol diethyl ether, tetrabutylene glycol diethyl ether, etc. Furthermore, these solvents may be used either solely or in combination of two or more thereof.

As the solvent for preparing a solution (catalyst liquid) of the Tebbe complex, a solvent such that a solubility of the Tebbe complex in 1 g of the solvent at 25° C. is more than 0.5 mmol/g is preferably used from the viewpoints of not causing deposition of the Tebbe complex during the storage and good operability. As the solvent such that the solubility of the Tebbe complex in 1 g of the solvent at 25° C. is more than 0.5 mmol/g, an aromatic hydrocarbon or an ether compound is preferably used. It is preferred that the thus-prepared solution of the Tebbe complex (catalyst liquid) is stored in a light-shielded vessel in the presence of an inert gas at 30° C. or lower.

The Tebbe complex that is obtained by the production method of the present invention is especially useful as a hydrogenation catalyst of an unsaturated double bond in the conjugated diene portion of an aromatic vinyl/conjugated diene block polymer. In addition, when the catalyst liquid is prepared using the Tebbe complex obtained by the production method of the present invention in the aforementioned manner and stored in a light-shielded vessel in the presence of an inert gas at 30° C. or lower, even after elapsing 4 months, the catalytic activity of the Tebbe complex does not substantially change, and the storage stability is extremely excellent.

EXAMPLES

The present invention is hereunder described in more detail by reference to Examples and so on, but it should be construed that the present invention is by no means limited by such Examples and so on.

An analysis method of a Tebbe reagent and a Tebbe complex used in the Examples and Comparative Examples is hereunder described.

<Yield of Tebbe Complex>

A molar concentration of a titanium atom in a solution (catalyst liquid) containing the Tebbe reagent or Tebbe complex was quantitatively determined by analyzing a wet decomposition product using a polarized Zeeman atomic absorption spectrophotometer (Z-2000 Model, manufactured by Hitachi, Ltd.).

A total molar amount of the titanium atom in the acquired catalyst liquid was calculated from the catalyst liquid mass and the molar concentration of a titanium atom in the catalyst liquid determined from the atomic absorption analysis.

A proportion of the total molar amount of the titanium atom in the acquired catalyst liquid relative to the charged molar amount of the titanium atom was defined as a yield (%) and calculated according to the following numerical expression (1). Each amount in the expression is mol.

Yield (%)=100×(Total molar amount of titanium atom in acquired catalyst liquid based on atomic absorption analysis)/(Charged molar amount of titanium atom) (1)

<Analysis Method of Purity>

The titanium compound existent in the catalyst liquid is a mixture of Titanium Compounds I-1 to I-6 having the following structures.

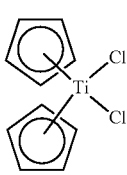
(I-1)

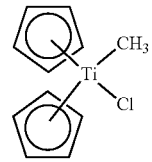
(I-2)

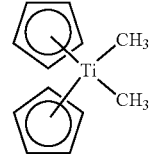
(I-3)

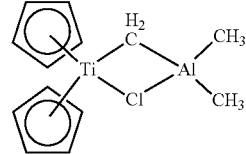
(I-4)

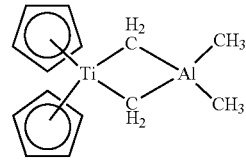
(I-5)

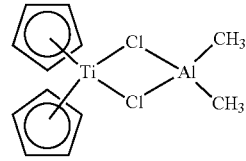
(I-6)

A solution of 0.3 g of a catalyst liquid diluted with 0.3 g of dehydrated deuterium benzene-$d_6$ was measured by the $^1$H-NMR measurement [nuclear magnetic resonance apparatus: JNM-ECS400, manufactured by JEOL Ltd.], each of Titanium Compounds I-1 to I-5 was subjected to structure assignment from a chemical shift, and a molar amount of the titanium atom forming the structure of each of Titanium Compounds I-1 to I-5 contained in 1 g of the catalyst liquid was calculated from a relative peak area value to benzene.

Since Titanium Compound I-6 is a paramagnetic nuclide, it was difficult to perform precise quantitative determination from a peak area value of $^1$H-NMR. Accordingly, a molar amount obtained by subtracting the molar amount of each of Titanium Compounds I-1 to I-5 which can be quantitatively determined by the $^1$H-NMR analysis from the molar amount of the titanium atom contained in 1 g of the catalyst liquid which can be quantitatively determined by the atomic absorption analysis was calculated as a molar amount of Titanium Compound I-6.

As described above, the molar amount of each of Titanium Compounds I-1 to I-6 contained in 1 g of the catalyst liquid became clear from the atomic absorption analysis and $^1$H-NMR analysis, and an Al/Ti ratio as a ratio of the aluminum atom to one titanium atom was calculated.

A proportion of the molar amount of the titanium atom of Titanium Compound I-4 as the Tebbe complex that is the metal complex according to the present invention relative to the total molar amount of the titanium atom in the catalyst liquid was defined as a purity (%) and calculated according to the following numerical expression (2). Each amount in the expression is mol.

Purity (%)=100×(Molar amount of titanium atom of Titanium Compound I-4 based on $^1$H-NMR analysis)/(Total molar amount of titanium atom in catalyst liquid based on atomic absorption analysis)         (2)

<Measurement of Solubility of Tebbe Complex>

The measurement of the solubility of the Tebbe complex in a solvent was performed in the following manner. That is, 4 mL of a solvent of every kind was added to 1 g of a Tebbe complex obtained in the following Preparation Example 1; a solution after stirring at 25° C. for one hour was filtered with a membrane filter of 0.2 μm; the filtrate was subjected to atomic absorption analysis using the aforementioned polarized Zeeman atomic absorption spectrophotometer; and a titanium atom concentration was measured.

[Preparation Example 1] (Preparation of Tebbe Complex for Test)

In a 200-mL volume three-neck flask equipped with a thermometer and a rotator, in which after drying under reduced pressure, the interior thereof had been purged with argon, 25.00 g (100.40 mmol) of bis(cyclopentadienyl) titanium dichloride ($Cp_2TiCl_2$, manufactured by Wako Pure Chemical Industries, Ltd.) and 20.00 g of hexane were added and stirred at 25±2° C. for 30 minutes. Subsequently, 150.0 mL of a hexane solution of trimethylaluminum (manufactured by Tokyo Chemical Industry Co., Ltd.) (201.6 mmol as trimethylaluminum) was added over 10 minutes, and the contents were allowed to react with each other at 25±3° C. for 60 hours. The resulting reaction liquid was cooled to 5° C. with water with ice, and a crystal was thoroughly deposited over one hour. A reaction liquid containing impurities was removed in an argon (Ar) atmosphere by means of decantation. 200 mL of hexane was added to the resulting brownish-red crystal; the contents were stirred for 30 minutes while cooling with water with ice; and the remaining unreacted trimethylaluminum and by-produced chlorodiethylaluminum were removed. Toluene was added to the resulting brownish-red crystal; the temperature was raised to 27° C.; the resultant was stirred for 30 minutes to completely dissolve the crystal; and impurities were then removed by means of filtration.

After confirming the concentration of Titanium Compound I-4 by $^1$H-NMR analysis of the resulting solution, the resultant was concentrated at 10 mmHg (1.33 kPa) and 30° C. and adjusted to 2.5 to 2.6% by mass in terms of a titanium atom concentration, thereby obtaining a catalyst liquid a1 of the Tebbe complex (hereinafter referred to simply as "Catalyst Liquid a1").

The Catalyst Liquid a1 was stored at 0° C. for 100 hours to deposit a brownish-red crystal b1; a supernatant solution was removed by means of decantation; the residue was heated to 30° C. under reduced pressure of 10 mmHg (1.33 kPa), thereby removing almost all of the solvent component; and the pressure within the system was then returned to atmospheric pressure with argon. The amount of the acquired brownish-red crystal b1 was 9.94 g, and the brownish-red crystal b1 was used for confirming the solubility in the solvent of every kind.

0.30 g of the brownish-red crystal b1 was dissolved in 1.74 g of toluene and subjected to atomic absorption analysis. As a result, this solution contained 2.50% by mass (concentration: 0.522 mmol/g) of the titanium atom. The amount of the titanium atom contained in 0.30 g of the brownish-red crystal b1 was 1.06 mmol, and a total mass of the brownish-red crystal b1 was 9.94 g. Thus, the brownish-red crystal b1 contained 35.121 mmol of the titanium atom. Meanwhile, in view of the fact that the bis(cyclopentadienyl)titanium dichloride ($Cp_2TiCl_2$, manufactured by Wako Pure Chemical Industries, Ltd.) used for the production of the Catalyst Liquid a1 was 25.00 g (100.400 mmol), the yield was 34.98%.

0.30 g of the brownish-red crystal b1 was dissolved in 1.74 g of toluene, and 0.3 g of this solution was subjected to $^1$H-NMR measurement within one hour. As a result, any peaks capable of being assigned to Titanium Compounds I-1, I-3, I-5, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.022 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ−0.11 ppm (6H, s); and the concentration was 0.500 mmol/g. The concentration of Titanium Compound I-6 obtained from the results of $^1$H-NMR analysis and atomic absorption analysis was less than 0.001 mmol/g. From the concentrations of Titanium Compounds I-1 to I-6, the brownish-red crystal b1 was a Tebbe complex having a purity of 95.8%, and its Al/Ti ratio was 0.958.

Test Example 1

The measurement of the solubility of the Tebbe complex in a solvent was performed in the following manner. That is, 4 mL of a solvent of every kind was added to 1 g of the Tebbe complex obtained in Preparation Example 1; a solution after stirring at 25° C. for one hour was filtered with a membrane filter of 0.2 μm; and the filtrate was subjected to atomic absorption analysis using the aforementioned polarized Zeeman atomic absorption spectrophotometer, thereby measuring a titanium atom concentration.

On the occasion of confirming the solubility in the solvent of every kind, all of the operations were carried out within a room set at 25° C. Using a glove box, 1.0 g of the brownish-red crystal b1 of the Tebbe complex obtained in the method of Preparation Example 1 was weighed in a 20-mL eggplant type flask in an argon atmosphere, and a rotator and 4 mL of dehydrated hexane were added, followed by stirring at 25° C. for one hour. Thereafter, the resultant was allowed to stand and then filtered with a membrane filter of 0.2 μm, and 1.0 g of a filtrate containing the Tebbe complex was subjected to atomic absorption analysis, thereby measuring the solubility of the Tebbe complex. The filtrate contained 1.05% by mass (concentration: 0.22 mmol/g) of a titanium atom, and the solubility of the Tebbe complex was 0.22 mmol/g.

In addition, any peaks capable of being assigned to Titanium Compounds I-1 to I-6 were observed by means of $^1$H-NMR measurement. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s). In addition, as for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ−0.11 ppm (6H, s). Therefore, the aforementioned titanium atom concentration is one converted as a mixture having structures of Titanium Compound I-2 and Titanium Compound I-4.

Test Example 2

The same operations as in Test Example 1 were carried out, except for using 4 mL of heptane in place of 4 mL of the hexane. A filtrate contained 1.01% by mass (concentration: 0.21 mmol/g) of a titanium atom, and the solubility of the Tebbe complex was 0.21 mmol/g.

Test Example 3

The same operations as in Test Example 1 were carried out, except for using 4 mL of dodecane in place of 4 mL of the hexane. A filtrate contained 0.57% by mass (concentration: 0.12 mmol/g) of a titanium atom, and the solubility of the Tebbe complex was 0.12 mmol/g.

Test Example 4

The same operations as in Test Example 1 were carried out, except for using 4 mL of 2-methylpentane in place of 4 mL of the hexane. A filtrate contained 1.01% by mass (concentration: 0.21 mmol/g) of a titanium atom, and the solubility of the Tebbe complex was 0.21 mmol/g.

Test Example 5

The same operations as in Test Example 1 were carried out, except for using 4 mL of 2-hexene in place of 4 mL of the hexane. A filtrate contained 1.29% by mass (concentration: 0.27 mmol/g) of a titanium atom, and the solubility of the Tebbe complex was 0.27 mmol/g.

Test Example 6

The same operations as in Test Example 1 were carried out, except for using 4 mL of cyclohexane in place of 4 mL of the hexane. A filtrate contained 2.15% by mass (concentration: 0.45 mmol/g) of a titanium atom, and the solubility of the Tebbe complex was 0.45 mmol/g.

Comparative Test Example 1

The same operations as in Test Example 1 were carried out, except for using 4 mL of benzene in place of 4 mL of the hexane. A filtrate contained 5.65% by mass (concentration: 1.18 mmol/g) of a titanium atom, and the solubility of the Tebbe complex was 1.18 mmol/g.

Comparative Test Example 2

The same operations as in Test Example 1 were carried out, except for using 4 mL of toluene in place of 4 mL of the hexane. A filtrate contained 4.45% by mass (concentration: 0.93 mmol/g) of a titanium atom, and the solubility of the Tebbe complex was 0.93 mmol/g.

Comparative Test Example 3

The same operations as in Test Example 1 were carried out, except for using 4 mL of p-xylene in place of 4 mL of the hexane. A filtrate contained 4.50% by mass (concentration: 0.94 mmol/g) of a titanium atom, and the solubility of the Tebbe complex was 0.94 mmol/g.

Comparative Test Example 4

The same operations as in Test Example 1 were carried out, except for using 4 mL of diisopropyl ether in place of 4 mL of the hexane. A filtrate contained 2.87% by mass (concentration: 0.60 mmol/g) of a titanium atom, and the solubility of the Tebbe complex was 0.60 mmol/g.

Comparative Test Example 5

The same operations as in Test Example 1 were carried out, except for using 4 mL of cyclopentyl methyl ether in place of 4 mL of the hexane. A filtrate contained 6.17% by mass (concentration: 1.29 mmol/g) of a titanium atom, and the solubility of the Tebbe complex was 1.29 mmol/g.

Comparative Test Example 6

The same operations as in Test Example 1 were carried out, except for using 4 mL of 1,4-dioxane in place of 4 mL of the hexane. A filtrate contained 6.84% by mass (concentration: 1.43 mmol/g) of a titanium atom, and the solubility of the Tebbe complex was 1.43 mmol/g.

Comparative Test Example 7

The same operations as in Test Example 1 were carried out, except for using 4 mL of tetrahydrofuran in place of 4 mL of the hexane. A filtrate contained 8.19% by mass (concentration: 1.71 mmol/g) of a titanium atom, and the solubility of the Tebbe complex was 1.71 mmol/g.

Comparative Test Example 8

The same operations as in Test Example 1 were carried out, except for using 4 mL of methylene chloride in place of 4 mL of the hexane. A filtrate contained 7.13% by mass (concentration: 1.49 mmol/g) of a titanium atom, and the solubility of the Tebbe complex was 1.49 mmol/g.

TABLE 1

| | Solvent species | Classification of solvent | Solubility of Tebbe complex *1 (mmol/g) |
|---|---|---|---|
| Test Example 1 | Hexane | Straight-chain saturated hydrocarbon compound having 6 carbon atoms | 0.22 |
| Test Example 2 | Heptane | Straight-chain saturated hydrocarbon compound having 7 carbon atoms | 0.21 |

TABLE 1-continued

|  | Solvent species | Classification of solvent | Solubility of Tebbe complex *1 (mmol/g) |
|---|---|---|---|
| Test Example 3 | Dodecane | Straight-chain saturated hydrocarbon compound having 12 carbon atoms | 0.12 |
| Test Example 4 | 2-Methylpentane | Branched saturated hydrocarbon compound having 6 carbon atoms | 0.21 |
| Test Example 5 | 2-Hexene | Straight-chain unsaturated hydrocarbon compound having 6 carbon atoms | 0.27 |
| Test Example 6 | Cyclohexane | Alicyclic saturated hydrocarbon compound having 6 carbon atoms | 0.45 |
| Comparative Test Example 1 | Benzene | Aromatic hydrocarbon compound having 6 carbon atoms | 1.18 |
| Comparative Test Example 2 | Toluene | Aromatic hydrocarbon compound having 7 carbon atoms | 0.93 |
| Comparative Test Example 3 | p-Xylene | Aromatic hydrocarbon compound having 8 carbon atoms | 0.94 |
| Comparative Test Example 4 | Diisopropyl ether | Branched ether compound having 6 carbon atoms | 0.60 |
| Comparative Test Example 5 | Cyclopentyl methyl ether | Ether compound having 6 carbon atoms | 1.29 |
| Comparative Test Example 6 | 1,4-Dioxane | Cyclic ether compound having 4 carbon atoms | 1.43 |
| Comparative Test Example 7 | Tetrahydrofuran | Cyclic ether compound having 4 carbon atoms | 1.71 |
| Comparative Test Example 8 | Methylene chloride | Halogenated hydrocarbon having 1 carbon atom | 1.49 |

*1: Titanium atom concentration relative to 1 g of solvent at 25° C.

According to Test Examples 1 to 6, in the aliphatic hydrocarbons which is a straight-chain, branched, or alicyclic hydrocarbon, or in which a part of the carbon-carbon single bonds is replaced by an unsaturated double bond, the titanium atom concentration, namely the solubility of the Tebbe complex in 1 g of the solvent at 25° C. is 0.5 mmol/g or less, and it is evident that these solvents can be used for the production method of the Tebbe complex of the present invention.

According to Comparative Test Examples 1 to 8, in the aromatic hydrocarbons and ether compounds, the titanium atom concentration, namely the solubility of the Tebbe complex in 1 g of the solvent at 25° C. is more than 0.5 mmol/g, and it is evident that these solvents are suitable for storing the Tebbe complex as the catalyst liquid.

Example 1

In a 200-mL volume three-neck flask equipped with a thermometer and a rotator, in which after drying under reduced pressure, the interior thereof had been purged with argon, 25.00 g (100.40 mmol) of bis(cyclopentadienyl) titanium dichloride ($Cp_2TiCl_2$, manufactured by Wako Pure Chemical Industries, Ltd.) and 20.00 g of hexane were added and stirred at 25±2° C. for 30 minutes. Subsequently, 150.0 mL of a hexane solution of trimethylaluminum (manufactured by Tokyo Chemical Industry Co., Ltd.) [201.6 mmol as trimethylaluminum, and 2 molecules to one molecule of bis(cyclopentadienyl)titanium dichloride] was added over 10 minutes, and the contents were allowed to react with each other at 25±3° C. for 60 hours under a such condition that the charged amount of bis(cyclopentadienyl)titanium dichloride to hexane was 0.951 mmol/g in terms of a titanium atom concentration. The resulting reaction liquid was cooled to 5° C. with water with ice, and a crystal was thoroughly deposited over one hour. A reaction liquid containing impurities was removed in an Ar atmosphere by means of decantation. 200 mL of hexane was added to the resulting brownish-red crystal; the contents were stirred for 30 minutes while cooling with water with ice; and the remaining unreacted trimethylaluminum and by-produced chlorodimethylaluminum were removed. Toluene was added to the resulting brownish-red crystal; the temperature was raised to 27° C.; the resultant was stirred for 30 minutes to completely dissolve the crystal; and impurities were then removed by means of filtration.

After confirming the concentration of Titanium Compound I-4 by $^1$H-NMR analysis of the resulting solution, the resultant was concentrated at 10 mmHg (1.33 kPa) and 30° C. and adjusted to 2.5 to 2.6% by mass in terms of a titanium atom concentration, thereby obtaining a catalyst liquid 1 (hereinafter referred to simply as "Catalyst Liquid 1"). A total time required from the reaction commencement until completion of the concentration adjustment was about 64 hours.

As a result of atomic absorption analysis, the Catalyst Liquid 1 contained 2.57% by mass (concentration: 0.537 mmol/g) of a titanium atom, and a total mass of the Catalyst Liquid 1 was 142.17 g. Thus, the yield was 76.0%.

The Catalyst Liquid 1 was subjected to $^1$H-NMR analysis within one hour from the completion of concentration adjustment. As a result, any peaks capable of being assigned to Titanium Compounds I-1, I-3, I-5, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.027 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ−0.11 ppm (6H, s); and the concentration was 0.503 mmol/g. The concentration of Titanium Compound I-6 obtained from the results of $^1$H-NMR analysis and atomic absorption analysis was 0.007 mmol/g. From the concentrations of Titanium Compounds I-1 to I-6, the purity was 93.7%, and the Al/Ti ratio was 0.950.

Example 2

In a 200-mL volume three-neck flask equipped with a thermometer and a rotator, in which after drying under reduced pressure, the interior thereof had been purged with argon, 150.0 mL of a hexane solution of trimethylaluminum (manufactured by Tokyo Chemical Industry Co., Ltd.) [201.6 mmol as trimethylaluminum, and 2 molecules to one molecule of bis(cyclopentadienyl)titanium dichloride] was added. Subsequently, 25.00 g (100.40 mmol) of bis(cyclopentadienyl)titanium dichloride in a solid state ($Cp_2TiCl_2$, manufactured by Wako Pure Chemical Industries, Ltd.) was added in an argon gas stream using a powder funnel. The contents were allowed to react with each other at 25±3° C. for 60 hours under a such condition that the charged amount of bis(cyclopentadienyl)titanium dichloride to hexane was 1.174 mmol/g in terms of a titanium atom concentration. The resulting reaction liquid was cooled to 5° C. with water with ice, and a crystal was thoroughly deposited over one hour. A reaction liquid containing impurities was removed in an Ar atmosphere by means of decantation. 200 mL of hexane was added to the resulting brownish-red crystal; the contents were stirred for 30 minutes while cooling with water with ice; and the remaining unreacted trimethylaluminum and by-produced chlorodimethylaluminum were removed. Toluene was added to the resulting brownish-red crystal; the temperature was raised to 27° C.; the resultant was stirred for 30 minutes to completely dissolve the crystal; and impurities were then removed by means of filtration.

After confirming the concentration of Titanium Compound I-4 by $^1$H-NMR analysis of the resulting solution, the resultant was concentrated at 10 mmHg (1.33 kPa) and 30° C. and adjusted to 2.5 to 2.6% by mass in terms of a titanium atom concentration, thereby obtaining a catalyst liquid 2 (hereinafter referred to simply as "Catalyst Liquid 2"). A total time required from the reaction commencement until completion of the concentration adjustment was about 64 hours.

As a result of atomic absorption analysis, the Catalyst Liquid 2 contained 2.57% by mass (concentration: 0.537 mmol/g), and a total mass of the Crystal Liquid 2 was 150.67 g. Thus, the yield was 80.6%.

The Catalyst Liquid 2 was subjected to $^1$H-NMR analysis within one hour from the completion of concentration adjustment. As a result, any peaks capable of being assigned to Titanium Compounds I-1, I-3, I-5, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.032 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ−0.11 ppm (6H, s); and the concentration was 0.493 mmol/g. The concentration of Titanium Compound I-6 obtained from the results of $^1$H-NMR analysis and atomic absorption analysis was 0.012 mmol/g. From the concentrations of Titanium Compounds I-1 to I-6, the purity was 91.8%, and the Al/Ti ratio was 0.940.

Example 3

In a 200-mL volume three-neck flask equipped with a thermometer and a rotator, in which after drying under reduced pressure, the interior thereof had been purged with argon, 25.00 g (100.40 mmol) of bis(cyclopentadienyl) titanium dichloride ($Cp_2TiCl_2$, manufactured by Wako Pure Chemical Industries, Ltd.) and 50.00 g of hexane were added and stirred at 25±2° C. for 30 minutes. Subsequently, 150.0 mL of a hexane solution of trimethylaluminum (manufactured by Tokyo Chemical Industry Co., Ltd.) [201.6 mmol as trimethylaluminum, and 2 molecules to one molecule of bis(cyclopentadienyl)titanium dichloride] was added over 10 minutes, and the contents were allowed to react with each other at 25±3° C. for 60 hours under a such condition that the charged amount of bis(cyclopentadienyl)titanium dichloride to hexane was 0.741 mmol/g in terms of a titanium atom concentration. The resulting reaction liquid was cooled to 5° C. with water with ice, and a crystal was thoroughly deposited over one hour. A reaction liquid containing impurities was removed in an Ar atmosphere by means of decantation. 200 mL of hexane was added to the resulting brownish-red crystal; the contents were stirred for 30 minutes while cooling with water with ice; and the remaining unreacted trimethylaluminum and by-produced chlorodimethylaluminum were removed. Toluene was added to the resulting brownish-red crystal; the temperature was raised to 27° C.; the resultant was stirred for 30 minutes to completely dissolve the crystal; and impurities were then removed by means of filtration.

After confirming the concentration of Titanium Compound I-4 by $^1$H-NMR analysis of the resulting solution, the resultant was concentrated at 10 mmHg (1.33 kPa) and 30° C. and adjusted to 2.5 to 2.6% by mass in terms of a titanium atom concentration, thereby obtaining a catalyst liquid 3 (hereinafter referred to simply as "Catalyst Liquid 3"). A total time required from the reaction commencement until completion of the concentration adjustment was about 64 hours.

As a result of atomic absorption analysis, the Catalyst Liquid 3 contained 2.49% by mass (concentration: 0.520 mmol/g), and a total mass of the Crystal Liquid 3 was 137.69 g. Thus, the yield was 71.3%.

The Catalyst Liquid 3 was subjected to $^1$H-NMR analysis within one hour from the completion of concentration adjustment. As a result, any peaks capable of being assigned to Titanium Compounds I-1, I-3, I-5, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.031 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ−0.11 ppm (6H, s); and the concentration was 0.473 mmol/g. The concentration of Titanium Compound I-6 obtained from the results of $^1$H-NMR analysis and atomic absorption analysis was 0.016 mmol/g. From the concentrations of Titanium Compounds I-1 to I-6, the purity was 90.9%, and the Al/Ti ratio was 0.940.

Comparative Example 1

In a 500-mL volume three-neck flask equipped with a thermometer and a rotator, in which after drying under reduced pressure, the interior thereof had been purged with argon, 5.00 g (20.08 mmol) of bis(cyclopentadienyl)titanium dichloride ($Cp_2TiCl_2$, manufactured by Wako Pure Chemical Industries, Ltd.) and 250.00 g of hexane were added and stirred at 25±2° C. for 30 minutes. Subsequently, 29.5 mL of a hexane solution of trimethylaluminum (manufactured by Tokyo Chemical Industry Co., Ltd.) [39.7 mmol as trimethylaluminum, and 2 molecules to one molecule of bis(cyclopentadienyl)titanium dichloride] was added over 10 minutes, and the contents were allowed to react with each other at 25±3° C. for 60 hours under a such condition that the charged amount of bis(cyclopentadienyl)titanium dichloride to hexane was 0.075 mmol/g in terms of a titanium atom concentration. The resulting reaction liquid was concentrated at 10 mmHg (1.33 kPa) and 30° C. for one hour; about 400 mL of a mixture containing unreacted trimethylaluminum, by-produced chlorodimethylaluminum, and hexane was distilled off, the pressure was then returned to atmospheric pressure with argon; about 10 mL of toluene was added to the residual liquid; the temperature was raised to 30° C.; and the contents were stirred for dissolution over 30 minutes, thereby obtaining a catalyst liquid C1 (hereinafter referred to simply as "Catalyst Liquid C1"). A total time required from the reaction commencement until completion of the concentration adjustment was about 64 hours.

The Catalyst Liquid C1 was subjected to $^1$H-NMR analysis within one hour from the completion of concentration adjustment. As a result, any peaks capable of being assigned to Titanium Compounds I-1, I-3, I-4, I-5, and I-6 could not be observed. As for Titanium Compound I-2, a peak capable of being assigned to the methyl group was observed at δ1.13 ppm (3H, s), and a peak capable of being assigned to the cyclopentadienyl ring was observed at 5.97 ppm (10H, s).

The charged amount of bis(cyclopentadienyl)titanium dichloride to hexane was 0.075 mmol/g in terms of a titanium atom concentration, and a catalyst liquid containing Titanium Compound I-4 was not obtained in a range where the titanium atom concentration was less than 0.1 mmol/g.

Comparative Example 2

In a 200-mL volume three-neck flask equipped with a thermometer and a rotator, in which after drying under reduced pressure, the interior thereof had been purged with argon, 25.00 g (100.40 mmol) of bis(cyclopentadienyl) titanium dichloride ($Cp_2TiCl_2$, manufactured by Wako Pure Chemical Industries, Ltd.) and 30.00 g of toluene were added and stirred at 25±2° C. for 30 minutes. Subsequently, 112.0 mL of a toluene solution of trimethylaluminum (manufactured by Tokyo Chemical Industry Co., Ltd.) [201.6 mmol as trimethylaluminum, and 2 molecules to one molecule of bis(cyclopentadienyl)titanium dichloride] was added over 10 minutes, and the contents were allowed to react with each other at 25±3° C. for 60 hours under a such condition that the charged amount of bis(cyclopentadienyl) titanium dichloride to toluene was 0.910 mmol/g in terms of a titanium atom concentration. The resulting reaction liquid was concentrated at 10 mmHg (1.33 kPa) and 30° C. for one hour; about 134 mL of a mixture containing unreacted trimethylaluminum, by-produced chlorodimethylaluminum, and toluene was distilled off; the pressure was then returned to atmospheric pressure with argon; about 50 mL of toluene was added to the residual liquid; the temperature was raised to 30° C.; and the concentrated residue was dissolved over 30 minutes. The resulting solution was cooled to 0° C. and stirred for one hour. As a result, a brownish-red crystal was deposited. A supernatant solution was removed by means of decantation; 46.00 g of toluene was added to 8.50 g of the resulting brownish-red crystal; the temperature was raised to 30° C.; and the resultant was stirred for dissolution for 30 minutes, thereby obtaining a catalyst liquid C2 (hereinafter referred to simply as "Catalyst Liquid C2"). A total time required from reaction commencement until completion of the concentration adjustment was about 64 hours.

As a result of atomic absorption analysis, the Catalyst Liquid C2 contained 2.57% by mass of a titanium atom (concentration: 0.537 mmol/g), and a total mass of the Catalyst Liquid C2 was 54.50 g. Thus, the yield was 29.1%.

The Catalyst Liquid C2 was subjected to $^1$H-NMR analysis within one hour from the completion of concentration adjustment. As a result, any peaks capable of being assigned to Titanium Compounds I-1, I-3, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.017 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ−0.11 ppm (6H, s); and the concentration was 0.496 mmol/g. As for Titanium Compound I-5, a peak capable of being assigned to the methylene group could be observed at δ7.88 ppm (2H, s), a peak capable of being assigned to the cyclopentadienyl ring could be observed at 65.85 ppm (10H, s), and a peak capable of being assigned to the dimethylaluminum group could be observed at δ−0.03 ppm (6H, s); and the concentration was 0.019 mmol/g. The concentration of Titanium Compound I-6 obtained from the results of $^1$H-NMR analysis and atomic absorption analysis was 0.005 mmol/g. From the concentrations of Titanium Compounds I-1 to I-6, the purity was 92.4%, and the Al/Ti ratio was 0.968.

Comparative Example 3

In a 100-mL volume three-neck flask equipped with a thermometer and a rotator, in which after drying under reduced pressure, the interior thereof had been purged with argon, 7.90 g (31.7 mmol) of bis(cyclopentadienyl)titanium dichloride ($Cp_2TiCl_2$, manufactured by Wako Pure Chemical Industries, Ltd.) and 21.50 g of toluene were added and stirred at 25±2° C. for 30 minutes. Subsequently, 35.0 mL of a toluene solution of trimethylaluminum (manufactured by Tokyo Chemical Industry Co., Ltd.) [63.0 mmol as trimethylaluminum, and 2 molecules to one molecule of bis(cyclopentadienyl)titanium dichloride] was added over 10 minutes, and the contents were allowed to react with each other at 25±3° C. for 60 hours under a such condition that the charged amount of bis(cyclopentadienyl)titanium dichloride to toluene was 0.681 mmol/g in terms of a titanium atom concentration, thereby obtaining a catalyst liquid C3 (hereinafter referred to simply as "Catalyst Liquid C3"). A total time required from commencement until completion of the reaction was about 60 hours.

As a result of atomic absorption analysis, the Catalyst Liquid C3 contained 2.60% by mass of a titanium atom (concentration: 0.543 mmol/g), and a total mass of the Catalyst Liquid C3 was 57.2 g. Thus, the yield was 98.0%.

The Catalyst Liquid C3 was subjected to $^1$H-NMR analysis within one hour from the completion of reaction. As a result, any peaks capable of being assigned to Titanium Compounds I-1, I-5, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.064 mmol/g. As for Titanium Compound I-3, a peak capable of being assigned to the methyl group could be observed at δ3.26 ppm (6H, s), and a peak capable of being assigned to the cyclopentadienyl ring could be observed at δ5.85 ppm (10H, s); and the concentration was 0.012 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the dimethylaluminum group could be observed at δ–0.11 ppm (6H, s); and the concentration was 0.304 mmol/g. The concentration of Titanium Compound I-6 obtained from the results of $^1$H-NMR analysis and atomic absorption analysis was 0.163 mmol/g. From the concentrations of Titanium Compounds I-1 to I-6, the purity was 56.0%, and from the charged amount of the chemical liquid, the Al/Ti ratio was 2.00.

The results of Examples 1 to 3 and Comparative Examples 1 to 3 are shown in Table 2.

yield and the purity. In addition, as compared with Comparative Example 3 that is concerned with a conventional production method of a Tebbe reagent, Examples 1 to 3 are high in the purity.

Example 4

The same operations as in Example 1 were carried out, except that in Example 1, the reaction time of 60 hours was changed to a reaction time of 44 hours, thereby obtaining a catalyst liquid 4 (hereinafter referred to simply as "Catalyst Liquid 4"). A total time required from the reaction commencement until completion of the concentration adjustment was about 48 hours.

As a result of atomic absorption analysis, the Catalyst Liquid 4 contained 2.57% by mass (concentration: 0.537 mmol/g) of a titanium atom, and a total mass of the Catalyst Liquid 4 was 137.49 g. Thus, the yield was 73.5%.

The Catalyst Liquid 4 was subjected to $^1$H-NMR analysis within one hour from the completion of concentration adjustment. As a result, any peaks capable of being assigned to Titanium Compounds I-1, I-3, and I-6 could not be observed. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.027 mmol/g. As for Titanium Compound I-4, a peak capable of being assigned to the methylene group could be observed at 68.49 ppm (2H, s), a peak capable of being assigned to the cyclopentadienyl ring could be observed at δ5.85 ppm (10H, s), and a peak capable of being assigned to the dimethylaluminum group could be observed at δ–0.11 ppm (6H, s); and the concentration was 0.500 mmol/g. As for Titanium Compound I-5, a peak capable of being assigned to the methylene group

TABLE 2

| | Solvent | Charged mount of Cp$_2$TiCl$_2$ to solvent *1 (mmol/g) | Yield (%) | Purity (%) | Concentration of each component in catalyst liquid (mmol/g) | | | | | | |
|---|---|---|---|---|---|---|---|---|---|---|---|
| | | | | | I-1 | I-2 | I-3 | I-4 | I-5 | I-6 | Total |
| Example 1 | Hexane | 0.951 | 76.0 | 93.7 | 0 | 0.027 | 0 | 0.503 | 0 | 0.007 | 0.537 |
| Example 2 | Hexane | 1.174 | 80.6 | 91.8 | 0 | 0.032 | 0 | 0.493 | 0 | 0.012 | 0.537 |
| Example 3 | Hexane | 0.741 | 71.3 | 90.9 | 0 | 0.031 | 0 | 0.473 | 0 | 0.016 | 0.520 |
| Comparative Example 1 | Hexane | 0.075 | — | Detection limit or less | — | — | — | — | — | — | — |
| Comparative Example 2 | Toluene | 0.910 | 29.1 | 92.4 | 0 | 0.017 | 0 | 0.496 | 0.019 | 0.005 | 0.537 |
| Comparative Example 3 | Toluene | 0.681 | 98.0 | 56.0 | 0 | 0.064 | 0.012 | 0.304 | 0 | 0.163 | 0.543 |

*1: Expressing the charged amount of bis(cyclopentadienyl)titanium dichloride to the solvent at the time of reaction in terms of a titanium atom concentration According to Examples 1 to 3, in a range where the charged amount of bis(cyclopentadienyl)titanium dichloride to hexane is 0.741 to 1.174 mmol/g in terms of a titanium atom concentration, the Tebbe complex having a purity of 90% or more can be acquired in a yield of 70% or more, and thus, it is evident that the present invention can be suitably carried out in a wide titanium atom concentration range. According to Comparative Example 1, in the case where the titanium atom concentration is 0.075 mmol/g, a value of which is less than 0.1 mmol/g, it is evident that the desired product can be no longer acquired.

On the other hand, as compared with Comparative Example 2 that is concerned with a general production method of a high-purity Tebbe complex, Examples 1 to 3 of the present invention are excellent in a balance between the could be observed at δ7.88 ppm (2H, s), a peak capable of being assigned to the cyclopentadienyl ring could be observed at δ5.85 ppm (10H, s), and a peak capable of being assigned to the dimethylaluminum group could be observed at δ–0.03 ppm (6H, s); and the concentration was 0.005 mmol/g. The concentration of Titanium Compound I-6 obtained from the results of $^1$H-NMR analysis and atomic absorption analysis was 0.005 mmol/g. From the concentrations of Titanium Compounds I-1 to I-6, the purity was 93.1%, and the Al/Ti ratio was 0.950.

The point of time when the concentration adjustment was completed was defined as 0 minute of the storage time, and the components of Titanium Compounds I-1 to I-6 in the liquid were analyzed in the same method as in Example 1. In the case of being stored at 8±2° C. under light shielding in an Ar atmosphere, a change with time of each of the components was confirmed. The results are shown in Table 3.

Comparative Example 4

The same operations as in Comparative Example 2 were carried out, except that in Comparative Example 2, the use amount of toluene was changed from 30 g to 8 g, and that the reaction time of 60 hours was changed to a reaction time of 46 hours, thereby obtaining a catalyst liquid C4 (hereinafter referred to simply as "Catalyst Liquid C4"). A total time required from the reaction commencement until completion of the concentration adjustment was about 48 hours.

As a result of atomic absorption analysis, the Catalyst Liquid C4 contained 2.94% by mass (concentration: 0.615 mmol/g), and the yield was 98.0%.

The Catalyst Liquid C4 was subjected to $^1$H-NMR analysis within one hour from the completion of concentration adjustment. As a result, any peaks capable of being assigned to Titanium Compounds 1-3, I-5, and I-6 could not be observed. As for Titanium Compound I-1, a peak capable of being assigned to the cyclopentadienyl ring could be observed at 6.04 ppm (10H, s), and the concentration was 0.005 mmol/g. As for Titanium Compound I-2, a peak capable of being assigned to the methyl group could be observed at δ1.13 ppm (3H, s), and a peak capable of being assigned to the cyclopentadienyl ring could be observed at 5.97 ppm (10H, s); and the concentration was 0.035 mmol/g. As for Titanium Compound I-4, a peak capable of being assigned to the methylene group could be observed at δ8.49 ppm (2H, s), a peak capable of being assigned to the cyclopentadienyl ring could be observed at δ5.85 ppm (10H, s), and a peak capable of being assigned to the methylaluminum chloride group could be observed at δ−0.11 ppm (6H, s); and the concentration was 0.455 mmol/g. The concentration of Titanium Compound I-6 obtained from the results of $^1$H-NMR analysis and atomic absorption analysis was 0.120 mmol/g. From the concentrations of Titanium Compounds I-1 to I-6, the purity was 74.0%. From the charged amount of the chemical liquid, the Al/Ti ratio was 2.00.

The point of time when the concentration adjustment was completed was defined as 0 minute of the storage time, and the components of Titanium Compounds I-1 to I-6 in the liquid were analyzed in the same method as in Example 1. In the case of being stored at 8±2° C. under light shielding in an Ar atmosphere, a change with time of each of the components was confirmed. The results are shown in Table 3.

Example 4 are all the same degree in a range of from 0.455 to 0.500 mmol/g at the storage time of 0 day. However, it is noted that as compared with Comparative Example 4, when stored at 8±2° C. under light shielding in an Ar atmosphere, Example 4 is substantially free from the change of composition in the Tebbe complex solution and excellent in storage stability.

<Evaluation of Catalytic Activity>

Using each of the catalytic liquids of the Tebbe complex obtained in Example 1 and Comparative Example 3, the catalytic activity of the Tebbe complex was evaluated, thereby confirming the storage stability according to a hydrogenation reaction of a styrene/butadiene-based polymer as mentioned below.

Production Example 1

After purging the interior of a 10-L volume autoclave made of HASTELLOY (a registered trademark), which was equipped with a thermometer, an electric heater, an electromagnetic induction stirrer, and a sampling port, with a nitrogen gas, 5,291.0 g of cyclohexane and 2.529 g of a cyclohexane solution of 1.33 mmol/g of sec-butyllithium (3.364 mmol as sec-butyllithium) were added, and the temperature was raised to 50° C. over 30 minutes while stirring at 500 rpm.

Subsequently, 99.1 g (951.33 mmol) of styrene was collectively added into the autoclave, the pressure was increased to 0.3 MPaG (gauge pressure, hereinafter the same) using a nitrogen gas, and the reaction was performed at a liquid temperature of 53±3° C. for one hour. Subsequently, 5.248 g of a cyclohexane solution of 0.29 mmol/g of N,N,N',N'-tetramethylethylenediamine (1.535 mmol as N,N,N',N'-tetramethylethylenediamine) was added into the autoclave, and 389.4 g (7,198.1 mmol) of butadiene was further added into the autoclave over 10 minutes. The pressure was increased to 0.4 MPaG using a nitrogen gas, and the reaction was performed at a liquid temperature of 53±3° C. for 3 hours. Subsequently, 99.1 g (951.33 mmol) of styrene was collectively added, the pressure was increased to 0.5 MPaG using a nitrogen gas, and the reaction was performed at a liquid temperature of 53±3° C. for 1.5 hours, thereby obtaining a reaction mixed liquid containing a living polymer.

After decreasing the pressure of the nitrogen gas into the reaction mixed liquid to 0.1 MPaG, the pressure was increased to 1.0 MPaG using a hydrogen gas, and the contents were treated at a liquid temperature of 53±3° C. for one hour, thereby obtaining 5,886.3 g of a solution containing Polymer A (hereinafter referred to simply as "Polymer Solution A").

TABLE 3

| Storage time | Example 4 (each component; mmol/g) | | | | | | Comparative Example 4 (each component; mmol/g) | | | | | |
|---|---|---|---|---|---|---|---|---|---|---|---|---|
| (day) | I-1 | I-2 | I-3 | I-4 | I-5 | I-6 | I-1 | I-2 | I-3 | I-4 | I-5 | I-6 |
| 0 | 0 | 0.027 | 0 | 0.500 | 0.005 | 0.005 | 0.005 | 0.035 | 0 | 0.455 | 0 | 0.120 |
| 3 | 0 | 0.025 | 0 | 0.499 | 0.015 | 0 | 0.013 | 0.012 | 0 | 0.464 | 0.021 | 0.104 |
| 7 | 0 | 0.027 | 0 | 0.499 | 0.015 | 0 | 0.009 | 0.023 | 0 | 0.453 | 0.020 | 0.110 |
| 30 | 0 | 0.027 | 0 | 0.498 | 0.015 | 0 | 0.022 | 0.011 | 0 | 0.398 | 0.059 | 0.125 |
| 60 | 0 | 0.026 | 0 | 0.494 | 0.015 | 0.002 | 0.024 | 0.007 | 0 | 0.373 | 0.075 | 0.135 |
| 120 | 0 | 0.026 | 0 | 0.495 | 0.015 | 0.001 | — | — | — | — | — | — |

The concentrations of Titanium Compound I-4 that is the desired product contained in each of the Catalyst Liquid 4 of Example 4 and the Catalyst Liquid C4 of Comparative In view of the fact that the content of the Polymer A was 587.5 g, the Polymer A concentration in the Polymer Solution A was 9.98% by mass, the lithium atom concentration was 0.5256 mmol/kg from the use amount of sec-butyllithium, and the butadiene unit content in the Polymer A was 66.3% by mass from the use amounts of butadiene and styrene.

5 g of acetone was added to 5 g of the Polymer Solution A, and methanol was further properly added to deposit and recover the Polymer A, followed by drying at 60° C. for one hour to acquire the Polymer A. A weight average molecular weight Mw and a molecular weight distribution Mw/Mn of the Polymer A as expressed in terms of standard polystyrene measured were determined by gel permeation chromatography (hereinafter referred to simply as "GPC"), and the content proportions of bonding modes of the conjugated diene (1,2-bond unit and 1,4-bond unit) were determined by $^1$H-NMR analysis. The measurements conditions are as follows.

[GPC Analysis]
 Apparatus: HLC-8320GPC EcoSEC System, manufactured by Tosoh Corporation
 Sample: A solution of 5 mg of a polymer dissolved in 10 mL of tetrahydrofuran
 Injection amount of sample: 1 μL
 Column: TSKgel SuperHZ4000, manufactured by Tosoh Corporation (inner diameter: 4.6 mm, length: 150 mm)
 Column temperature: 40° C.
 Eluant: Tetrahydrofuran
 Flow rate of eluant: 1.0 mL/min
 Detector: UV detector (detection wavelength: 254 nm)
 Calibration curve: Prepared using standard polystyrene

[$^1$H-NMR Analysis]
 Apparatus: AVANCE III 600 USPlus, manufactured by Bruker BioSpin
 Sample: A solution of 50 mg of a polymer dissolved in 1.0 g of deuterium chloroform
 Standard substance: Tetramethylsilane
 Measurement temperature: 32° C. (305K)
 Cumulated number: 256 times A proportion [degree of vinylation (%)] of the branched bond modes relative to a total molar amount of the conjugated dienes contained in the polymer was calculated according to the following numerical expression (3).

Degree of vinylation (%)=100×(Molar amount of conjugated dienes having branched bond modes)/(Total molar amount of conjugated dienes)  (3)

As a result of the GPC analysis, the weight average molecular weight Mw of the Polymer A was 303,100, and the molecular weight distribution Mw/Mn was 1.06. The $^1$H-NMR analysis revealed that according to area values of a peak δ4.8 to 5.1 ppm capable of being assigned to the 1,2-bond unit 2H of butadiene and a peak δ5.2 to 5.5 ppm capable of being assigned to the 1,4-bond unit 2H of butadiene, the degree of vinylation of the Polymer A was 38.5%.

Evaluation Example 1

The interior of a 3-L volume SUS316-made autoclave equipped with a thermometer, an electric heater, an electromagnetic induction stirrer, a hydrogen supply port, a supply port of the Polymer Solution A, a 10-mL glass-made pressure bottle, and a sampling port was purged with a hydrogen gas. 750 g of the Polymer Solution A (containing 73.866 g of the Polymer A) was sent under pressure using a hydrogen gas, and the temperature was then raised to 75° C. for about 20 minutes while stirring at 500 rpm. Here, 15.684 g of a solution obtained by diluting polymethylhydrosiloxane having a number average molecular weight of 1,700 to 3,200 with cyclohexane (manufactured by Sigma-Aldrich) to an extent of 0.0742 mmol/g in terms of a silicon atom content (1.164 mmol as the silicon atom) was added thereto; the pressure was increased to 0.8 MPaG using a hydrogen gas; subsequently, 15.950 g of a solution obtained by diluting the Catalyst Liquid 1 having been stored at 8±2° C. for 5 days with cyclohexane to an extent of 2.89×10$^{-4}$ mmol/g as a titanium atom (4.61×10$^{-3}$ mmol as the titanium atom) was sent under pressure (1.0 MPaG) using a hydrogen gas and supplied from a 10-mL glass-made pressure bottle; and the liquid temperature was controlled to a range of 75±2° C. while supplying hydrogen so as to keep the internal pressure of the autoclave at 1.0 MPaG, thereby performing the hydrogenation reaction.

The state of progress of the hydrogenation reaction was analyzed in the following manner. That is, the point of time when the supply of the Catalyst Liquid 1 into the reaction system was completed was defined as 0 minute of the reaction commencement, and after elapsing 15 minutes, 30 minutes, 1 hour, 2 hours, 3 hours, 4 hours, 5 hours, 7 hours, and 9 hours, respectively, 5 g of the reaction liquid was sampled; 5 g of acetone and properly methanol were added to deposit and recover the Polymer A during the hydrogenation reaction; a $^1$H-NMR spectrum of a solution obtained by dissolving 50 mg of the recovered Polymer A in 1 g of deuterium chloroform was measured in the same manner as the measurement of the Polymer A; and from an integrated value of peaks at δ4.8 to 5.1 ppm capable of being assigned to the 1,2-bond unit based on butadiene and δ5.2 to 5.5 ppm capable of being assigned to the 1,4-bond unit based on butadiene, the content of a non-hydrogenated carbon-carbon double bond was quantitatively determined. A proportion of the total molar amount of the conjugated dienes consumed by the hydrogenation reaction to the total molar amount of the conjugated dienes before the reaction per kg of the Polymer A was defined as hydrogenation rate (%), and the hydrogenation rate was calculated according to the following numerical expression (4). A change with time of the hydrogenation rate is shown in Table 4. A change of the integrated value of peaks at δ6.2 to 7.5 ppm capable of being assigned to the hydrogen atom bonded to the aromatic ring of styrene was simultaneously observed. However, no change was found.

Hydrogenation rate (%)=100×{(Total molar amount of conjugated dienes before hydrogenation)−(Total molar amount of conjugated dienes after hydrogenation)}/(Total molar amount of conjugated dienes before hydrogenation)  (4)

Evaluation Example 2

The same operations as in Evaluation Example 1 were carried out, except that in Evaluation Example 1, the Catalyst Liquid 1 having been stored at 8±2° C. for 120 days was used in place of the Catalyst Liquid 1 having been stored at 8±2° C. for 5 days. The hydrogenation rate is shown in Table 4.

Comparative Evaluation Example 1

The same operations as in Evaluation Example 1 were carried out, except that in Evaluation Example 1, 15.95 g of a solution obtained by diluting the Catalyst Liquid C3 having been stored at 8±2° C. for 2 days with cyclohexane to an extent of 2.89×10$^{-4}$ mmol/g as a titanium atom (4.62×10$^{-3}$ mmol as the titanium atom) was used in place of the Catalyst Liquid 1 having been stored at 8±2° C. for 5 days. The hydrogenation rate is shown in Table 4.

TABLE 4

|  |  | Evaluation Example 1 | Evaluation Example 2 | Comparative Evaluation Example 1 |
|---|---|---|---|---|
| Catalyst Liquid | | 1 | 1 | C3 |
| Number of days of storage | | 5 | 120 | 2 |
| Hydrogenation rate for every reaction time (%) | 15 min | 8.6 | 7.8 | 5.3 |
| | 30 min | 18.8 | 17.4 | 10.7 |
| | 1 hr | 42.6 | 39.7 | 22.5 |
| | 2 hr | 97.6 | 97.0 | 58.3 |
| | 4 hr | 99.6 | 99.2 | 96.1 |
| | 5 hr | — | — | 98.1 |

From Evaluation Examples 1 to 2, it is noted that the Tebbe complex obtained by the production method of the present invention was excellent in the storage stability, and that the hydrogenation catalytic activity of the Catalyst Liquid 1 did not change even after the storage of 120 days. In addition, from Evaluation Examples 1 to 2 and Comparative Example 1, it is noted that as compared with the case of using the conventional Tebbe reagent (C3), the Catalyst Liquid 1 is high in the hydrogenation catalytic activity per one titanium atom.

INDUSTRIAL APPLICABILITY

In accordance with present invention, a high-purity Tebbe complex can be industrially advantageously produced in a high yield. Furthermore, the solution of the Tebbe complex obtained by the production method of the present invention can be stored over a long period of time without adding an additive, such as a stabilizer, etc., and has high catalytic activity per one titanium atom as compared with a conventional Tebbe reagent, so that it is possible to reduce the use amount of a catalyst. Thus, the present invention is high in industrial value. That is, according to the present invention, a Tebbe complex having a purity of 90% or more can be produced in a yield of 70% or more. In view of the fact that as compared with a conventional Tebbe reagent, the Tebbe complex that can be produced by the present invention is high with respect to the catalytic activity per one titanium atom, it is possible to reduce the use amount of a catalyst. Furthermore, it is possible to stably store the Tebbe complex which can be produced by the present invention for 120 days or more in an inert gas atmosphere without making an oxygen-containing organic compound having 2 or more carbon atoms or a nitrogen-containing compound or a compound composed of a salt thereof coexistent.

The invention claimed is:

1. A method for producing a Tebbe complex, the method comprising
reacting bis(cyclopentadienyl)titanium dichloride with trimethylaluminum in the presence of a solvent such that a solubility of the Tebbe complex in 1 g of the solvent at 25° C. is 0.5 mmol/g or less, thereby obtaining a reaction liquid,
wherein a charged amount of the bis(cyclopentadienyl) titanium dichloride is from 0.1 to 2.5 mmol/g in terms of a titanium atom concentration relative to the solvent.

2. The method according to claim 1, wherein the solvent is an aliphatic hydrocarbon having 3 to 20 carbon atoms.

3. The method according to claim 2, wherein the aliphatic hydrocarbon having 3 to 20 carbon atoms is at least one selected from the group consisting of a straight-chain aliphatic hydrocarbon having 3 to 20 carbon atoms and a branched aliphatic hydrocarbon having 3 to 20 carbon atoms.

4. The method according to claim 1, wherein a charged amount of the trimethylaluminum is one to twenty molecules relative to one molecule of the bis(cyclopentadienyl) titanium dichloride.

5. The method for producing a Tebbe complex according to claim 1, wherein said reacting is performed at a temperature of from 0 to 125° C.

6. The method for producing a Tebbe complex according to claim 1, wherein said reacting is performed for a time of from 1 to 200 hours.

7. The method for producing a Tebbe complex according to claim 1, further comprising
recovering the Tebbe complex in a solid state as deposited from the reaction liquid by filtration or decantation.

8. The method according to claim 1, further comprising concentrating the reaction liquid at a concentration temperature of 10 to 125° C. under a pressure of 0.001 to 0.100 MPaG.

9. The method according to claim 1, further comprising subjecting the reaction liquid to a crystallization operation at a crystallization temperature of −10 to 20° C. for a time of 30 minutes or more.

10. The method according to claim 1, further comprising washing the Tebbe complex with a hydrocarbon solvent, wherein the hydrocarbon solvent has a dielectric constant of 1.0 to 5.0.

11. The method according to claim 1, further comprising storing the Tebbe complex in the presence of a solvent such that a solubility of the Tebbe complex in 1 g of the solvent at 25° C. is more than 0.5 mmol/g.

* * * * *